United States Patent
Kim et al.

(10) Patent No.: US 11,673,965 B2
(45) Date of Patent: Jun. 13, 2023

(54) METHOD OF TREATING METASTATIC TRIPLE NEGATIVE BREAST CANCER WITH RADIOTHERAPY COMBINED WITH PHOSPHATIDYL INOSITOL-3 KINASE DELTA/GAMMA INHIBITORS AND ANTI-PD-1 ANTIBODIES

(71) Applicant: Seoul National University R&DB Foundation, Seoul (KR)

(72) Inventors: In-Ah Kim, Seongnam-si (KR); Min-Guk Han, Gwangju-si (KR); Bum-Sup Jang, Seongnam-si (KR); Mi-Hyun Kang, Seongnam-si (KR); Won-Ick Chang, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 406 days.

(21) Appl. No.: 16/920,933

(22) Filed: Jul. 6, 2020

(65) Prior Publication Data

US 2021/0198378 A1 Jul. 1, 2021

(30) Foreign Application Priority Data

Dec. 31, 2019 (KR) .................. 10-2019-0180060

(51) Int. Cl.
*C07K 16/30* (2006.01)
*A61P 35/04* (2006.01)
*A61K 45/06* (2006.01)
*A61K 31/52* (2006.01)
*C07K 16/28* (2006.01)

(52) U.S. Cl.
CPC .......... *C07K 16/3015* (2013.01); *A61K 31/52* (2013.01); *A61P 35/04* (2018.01); *C07K 16/2818* (2013.01); *A61K 45/06* (2013.01)

(58) Field of Classification Search
CPC .... A61K 35/04; A61K 31/12; C07K 16/3015; C07K 16/2818
See application file for complete search history.

(56) References Cited

FOREIGN PATENT DOCUMENTS

| KR | 10-2010-0016354 | 2/2010 | |
|---|---|---|---|
| KR | 10-2017-0015460 | 2/2017 | |
| KR | 10-2019-0007488 | 1/2019 | |
| WO | WO2015193352 | * 12/2015 | ............... A61N 5/10 |

OTHER PUBLICATIONS

Ma et al., Discovery of novel quinazolinone derivatives as high potent and selective PI3Kδ and PI3Kδγ inhibitors. European Journal of Medicinal Chemistry 151, 9-17, 2018. (Year: 2018).*
Jun Gong et al., "Radiation therapy and PD-1/PD-L1 blockade: the clinical development of an evolving anticancer combination", Journal for ImmunoTherapy of Cancer (2018) 6:46, Jun. 4, 2018.
Sebastian Hasslacher et al., "Inhibition of PI3K signalling increases the efficiency of radiotherapy in glioblastoma cells", International Journal of Oncology 53: pp. 1881-1896, 2018 , Aug. 16, 2018.
Jiqing Sai et al., "PI3K Inhibition Reduces Mammary Tumor Growth and Facilitates Antitumor Immunity and Anti-PD1 Responses", Clinical Cancer Res 23(13) pp. 3371-3384 (2016), Dec. 21, 2016.
Na Young Jang et al., "Radiosensitization with combined use of olaparib and PI-103 in triple-negative breast cancer", BMC Cancer (2015) 15:89, Mar. 3, 2015.
Gulidanna Shayan et al., "Adaptive resistance to anti-PD1 therapy by Tim-3 upregulation is mediated by the PI3K-Akt pathway in head and neck cancer", Oncoimmunology. 2017, vol. 6, No. 1, e1261779 (11 pages), Jan. 10, 2017.

* cited by examiner

*Primary Examiner* — Elly-Gerald Stoica
(74) *Attorney, Agent, or Firm* — Lex IP Meister, PLLC

(57) ABSTRACT

The present invention provides a pharmaceutical composition and a treatment method to be combined with radiotherapy, for treatment of triple negative breast cancer. More specifically, the pharmaceutical composition comprises a PD-1 blockade and a PI3Kγ δ inhibitor, and it has excellent effects of inhibiting tumor and enhancing immunity by combining the PD-1 blockade and PI3Kγ δ inhibitor with radiotherapy, compared to single therapy of each therapeutic agent.

7 Claims, 16 Drawing Sheets

[FIG. 1a]
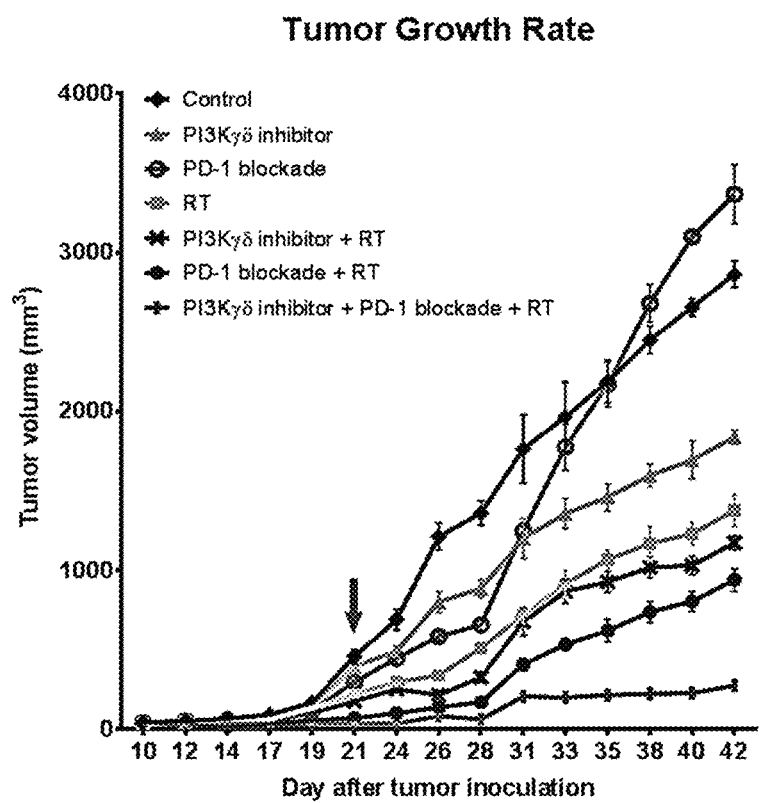
[FIG. 1b]
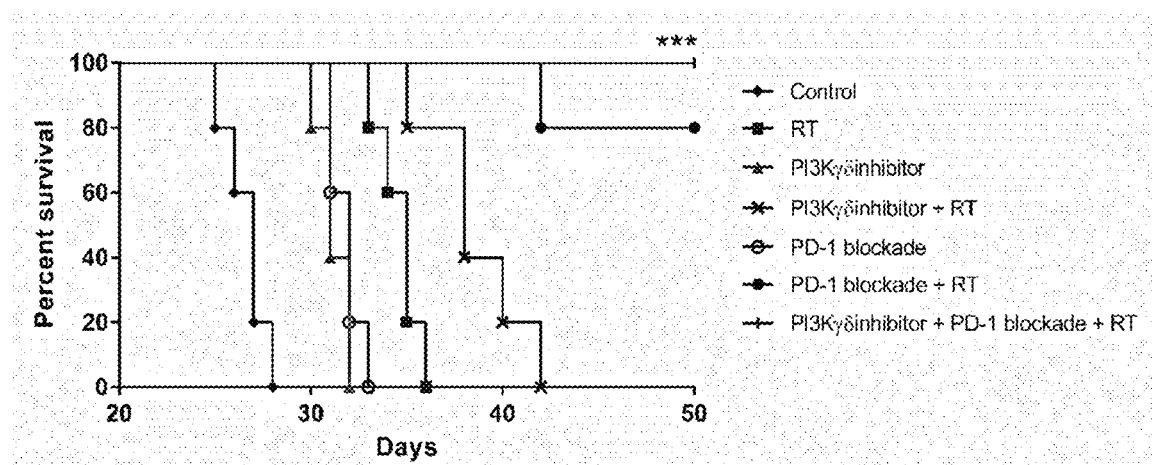

[FIG.2a]
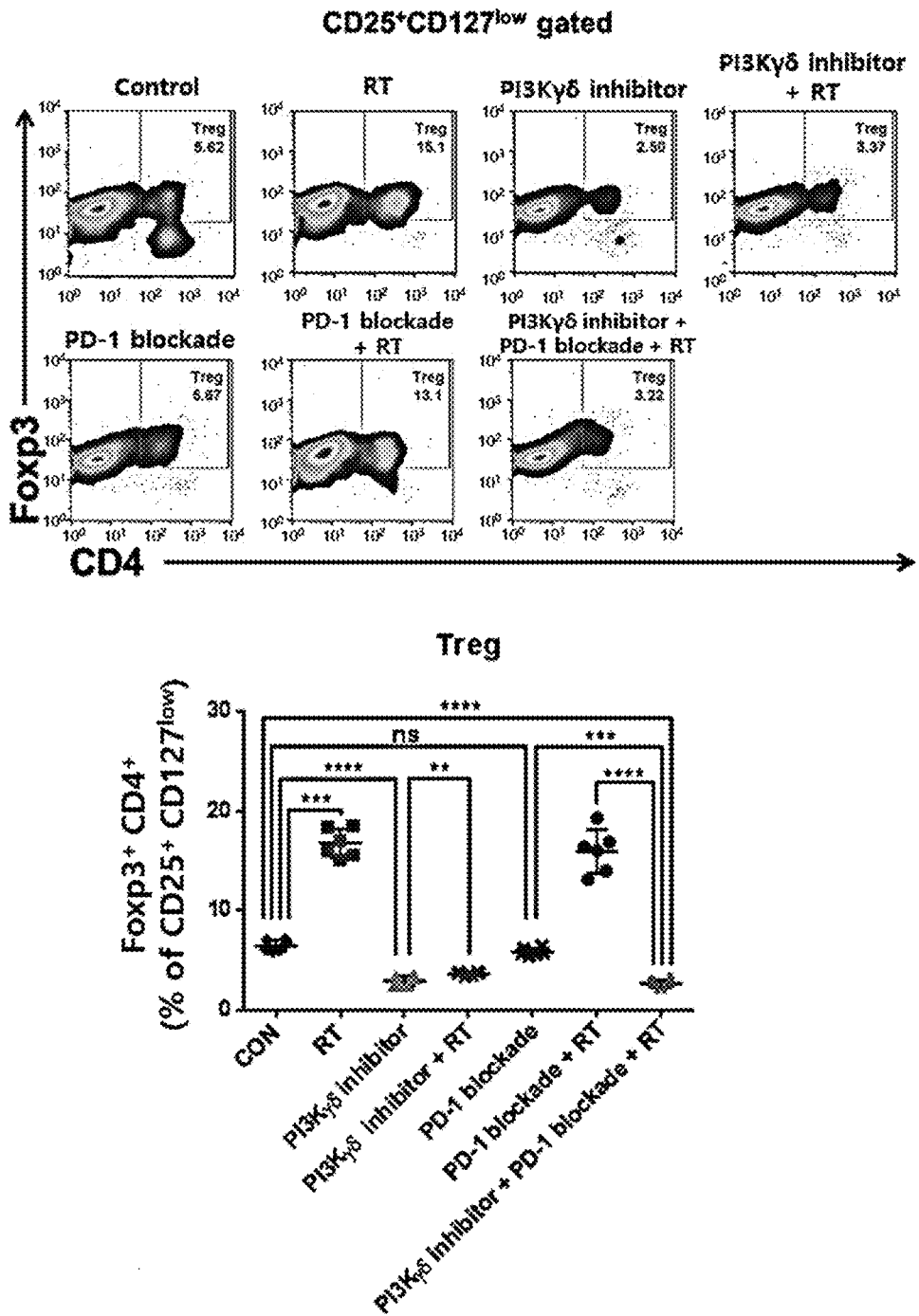

[FIG.2b]
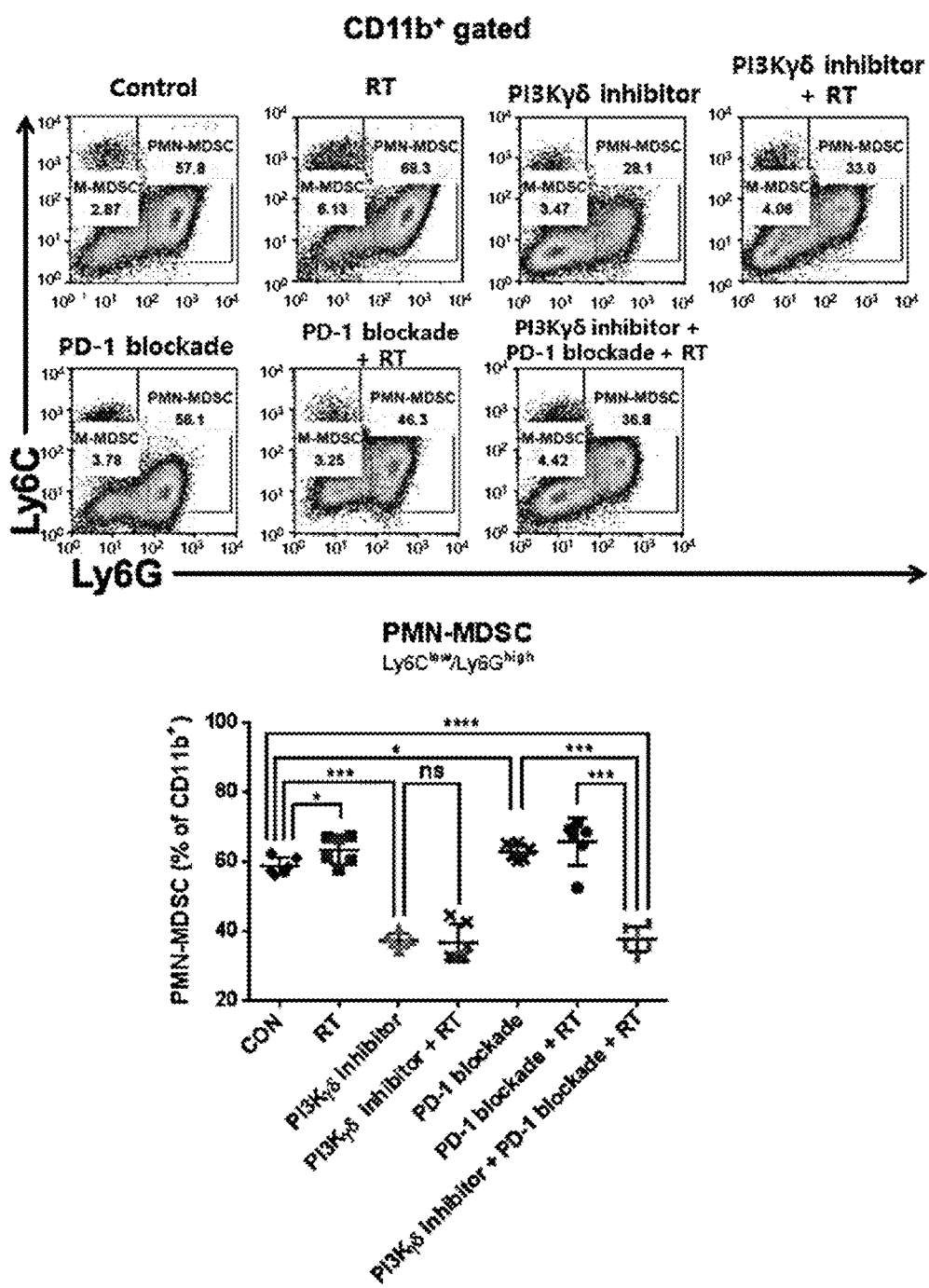

[FIG.2c]
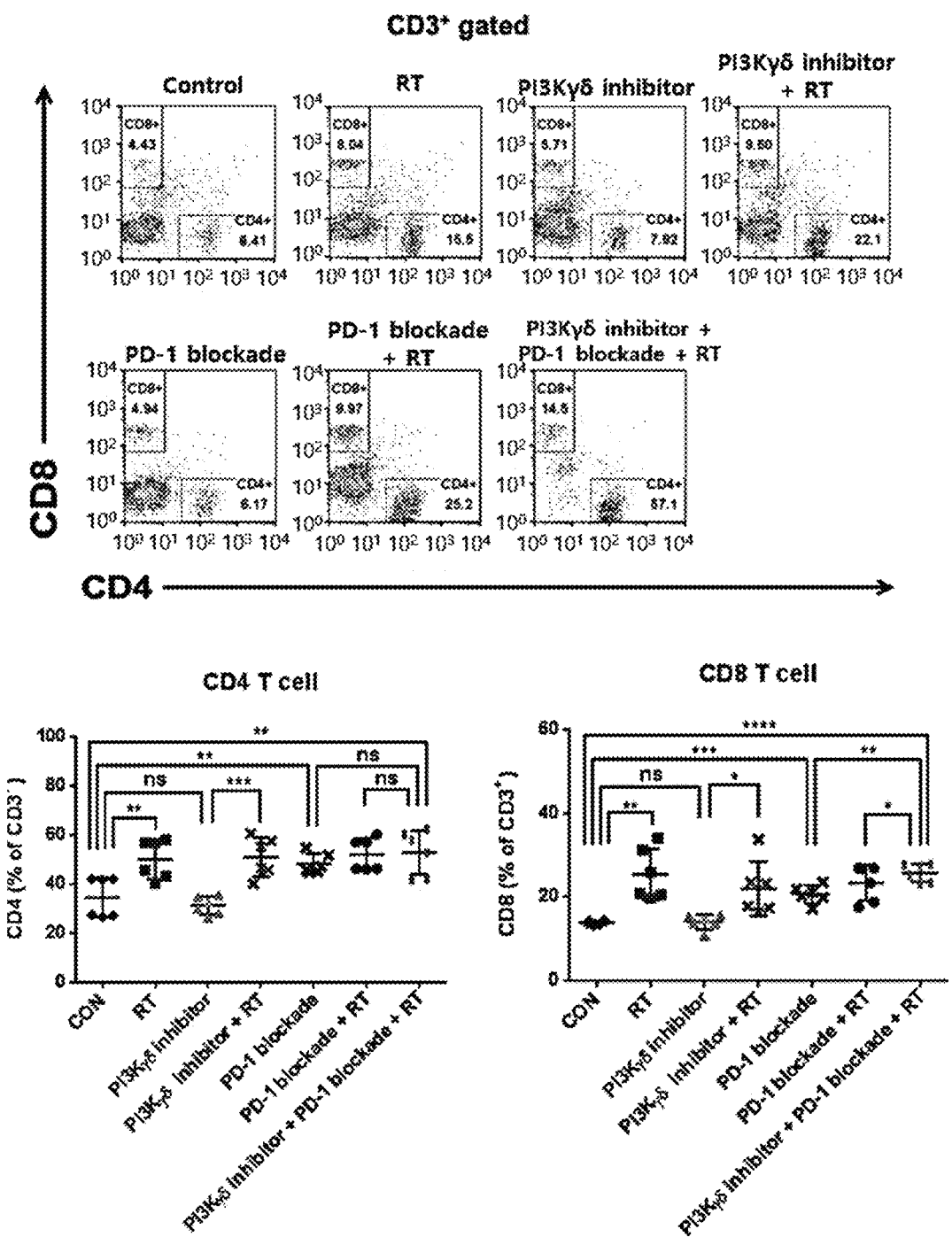

[FIG.3a]
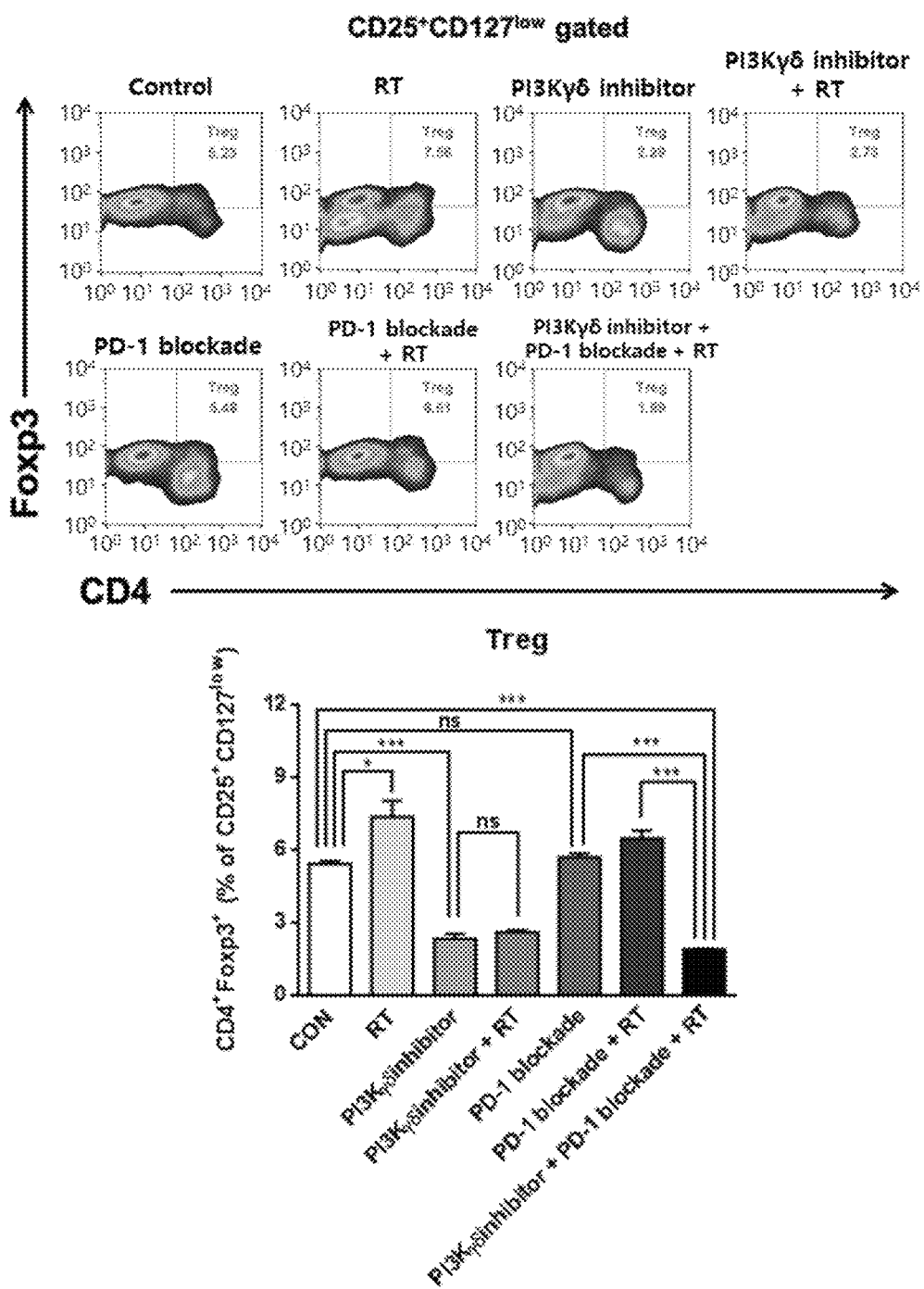

[FIG.3b]
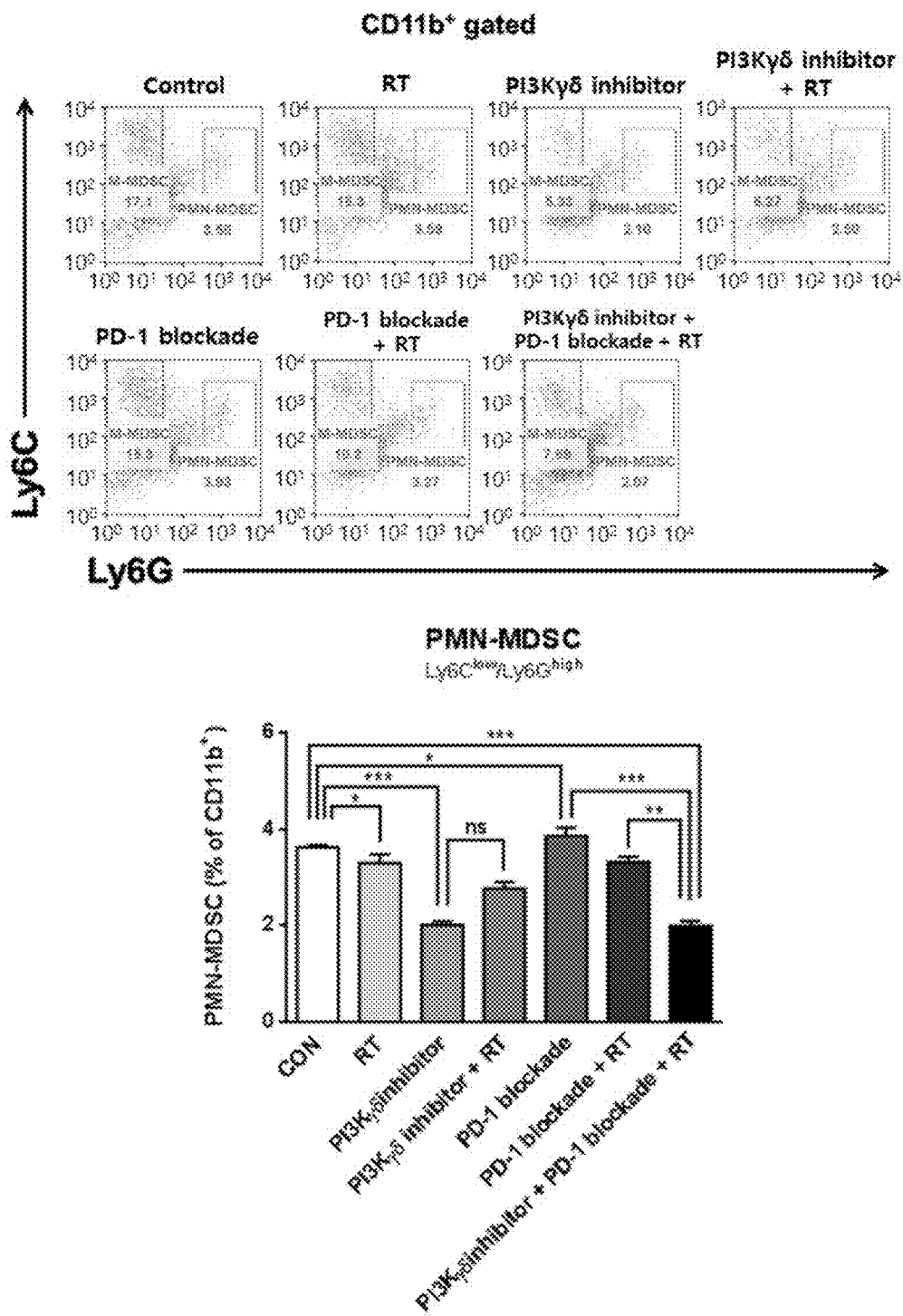

[FIG.3c]
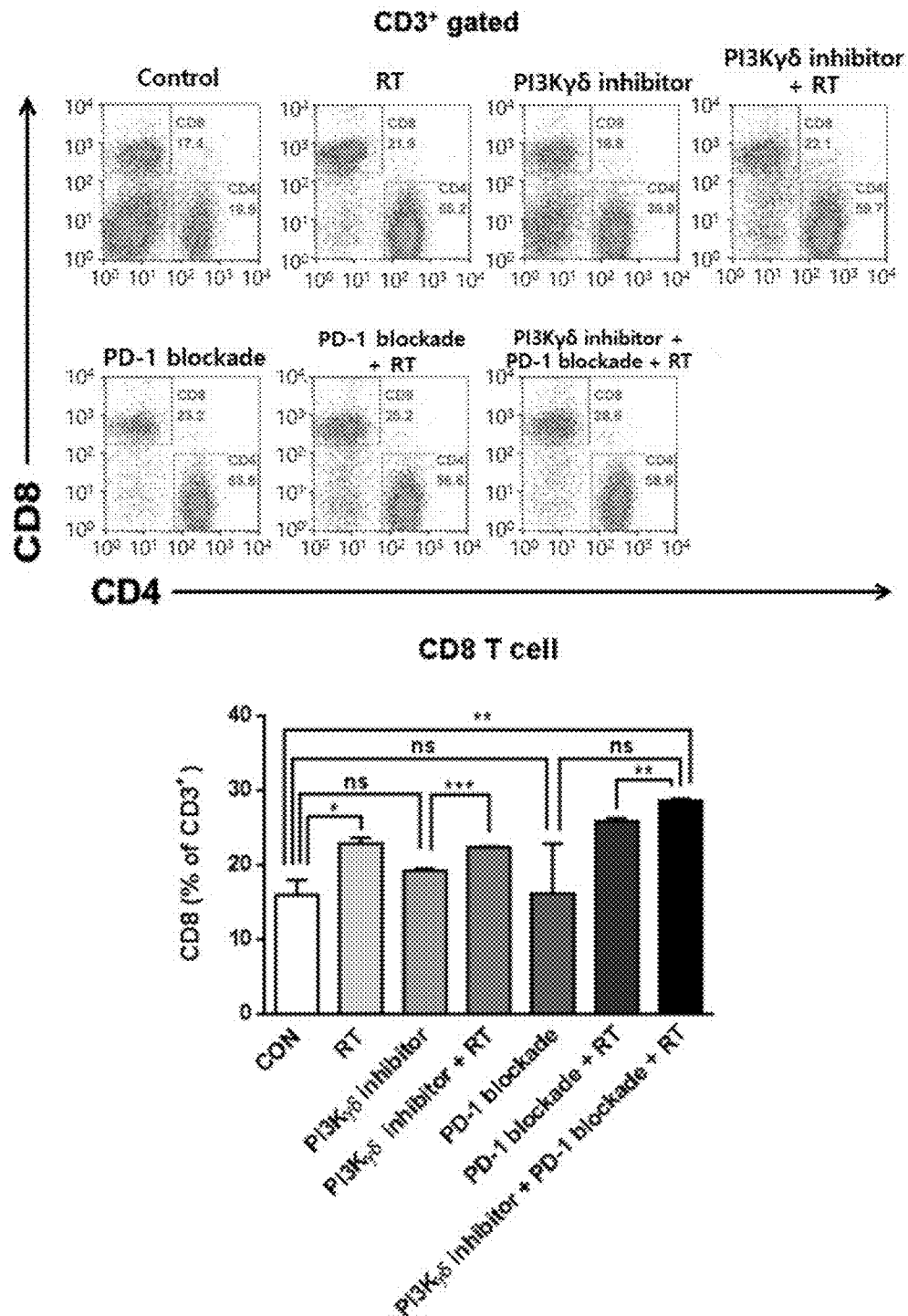

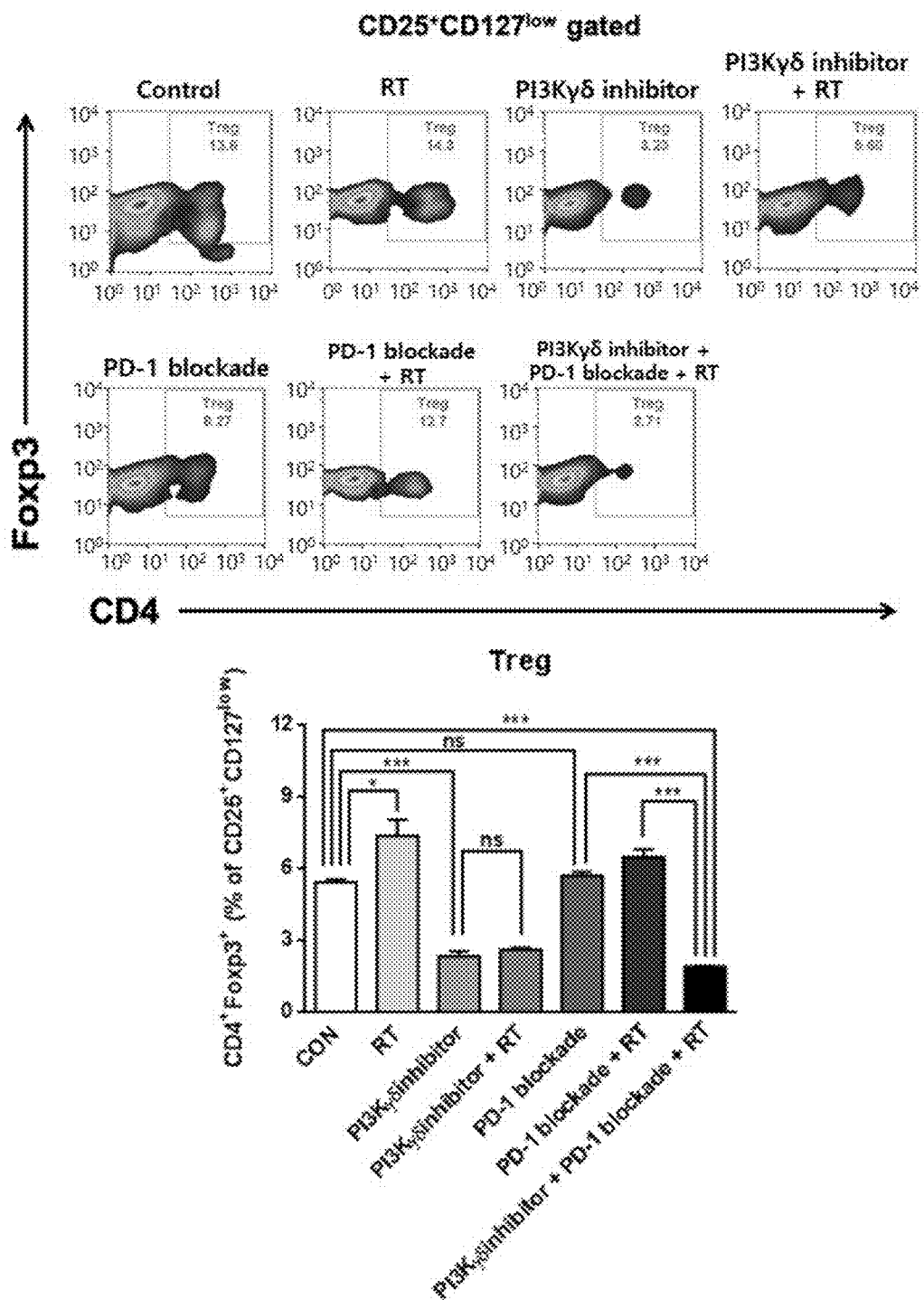
[FIG.4a]

[FIG.4b]
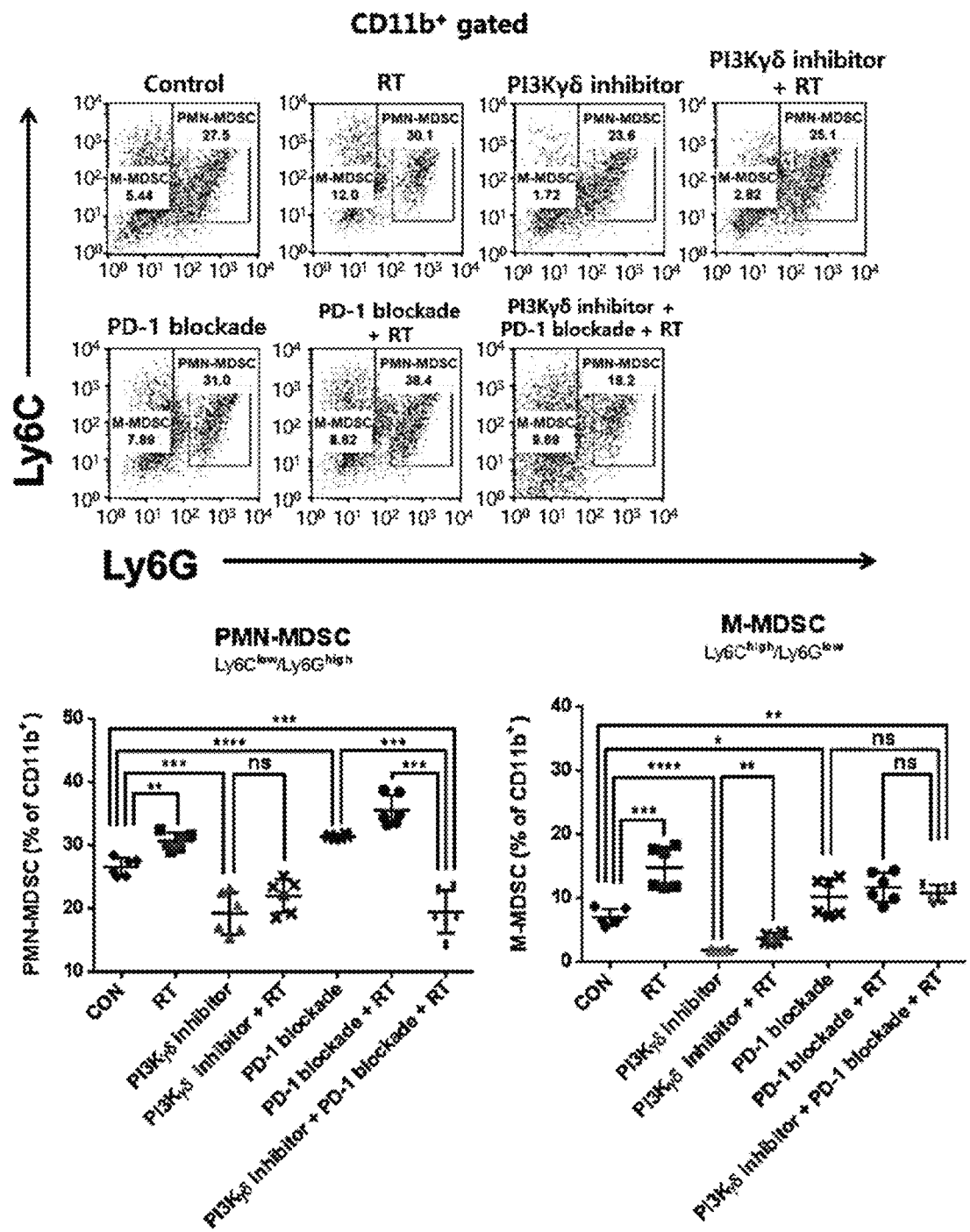

[FIG.4c]
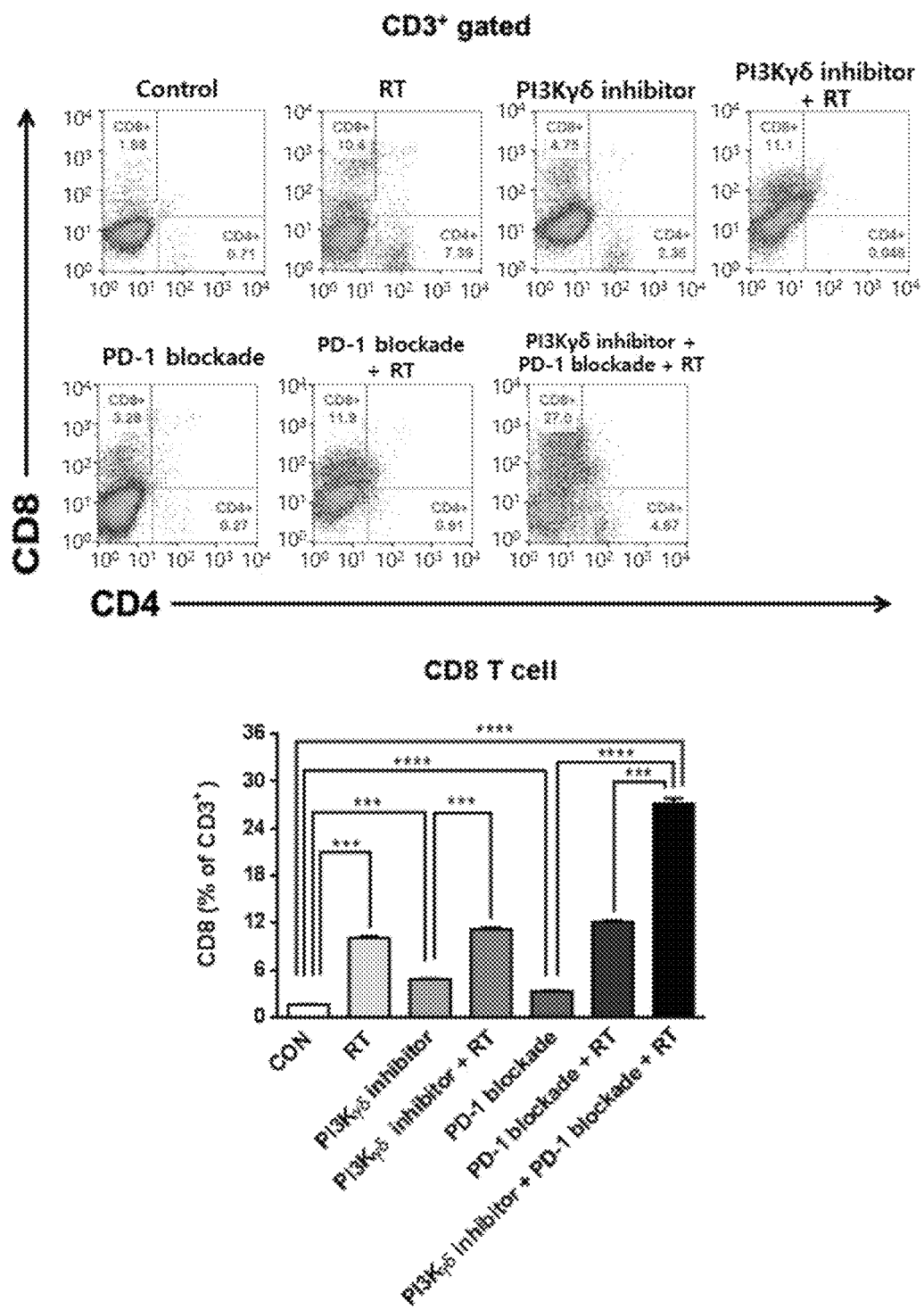

[FIG.5]
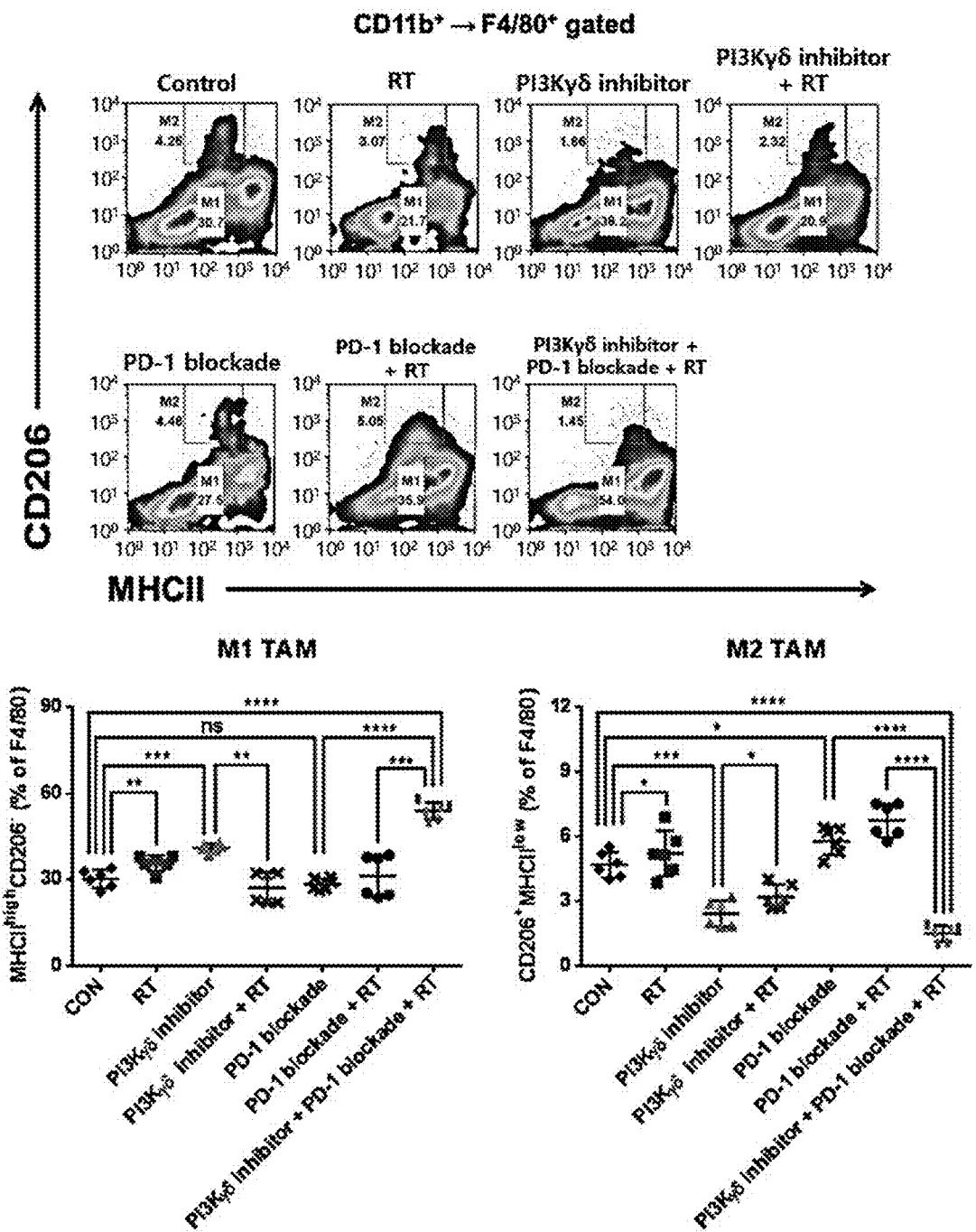

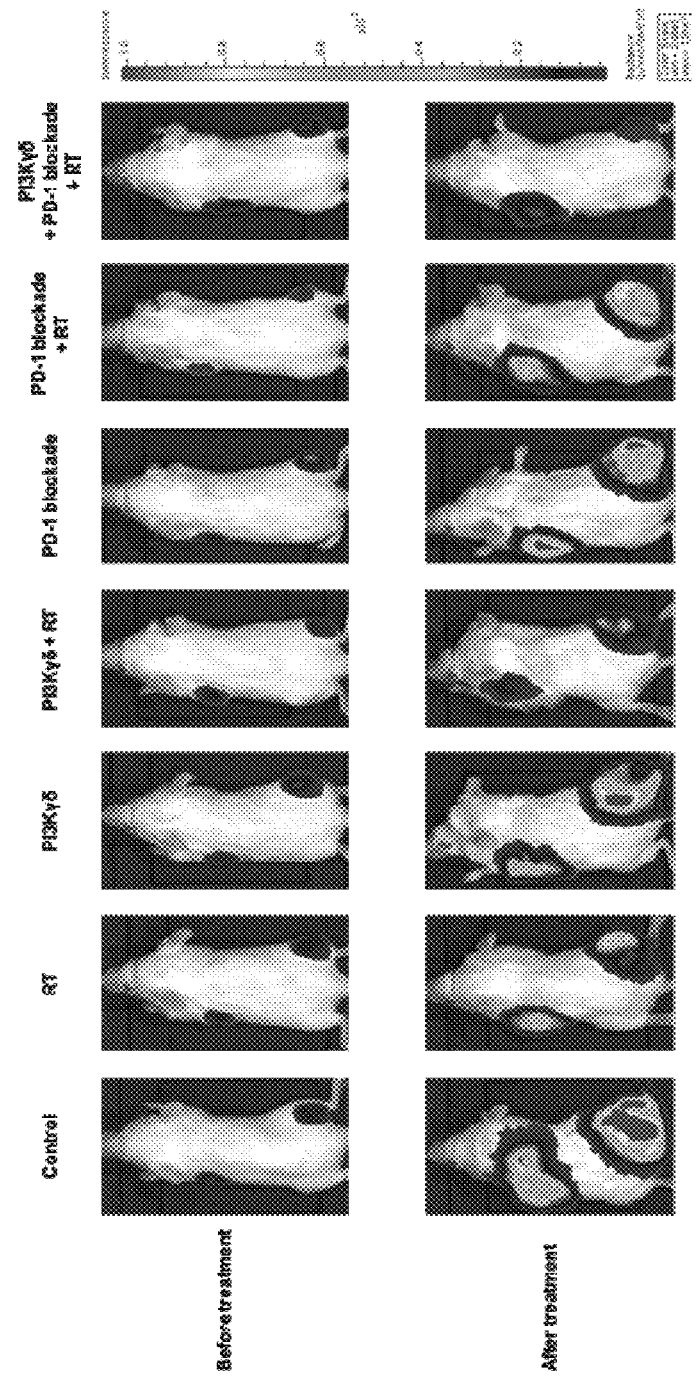
[FIG. 6a]

[FIG. 6b]
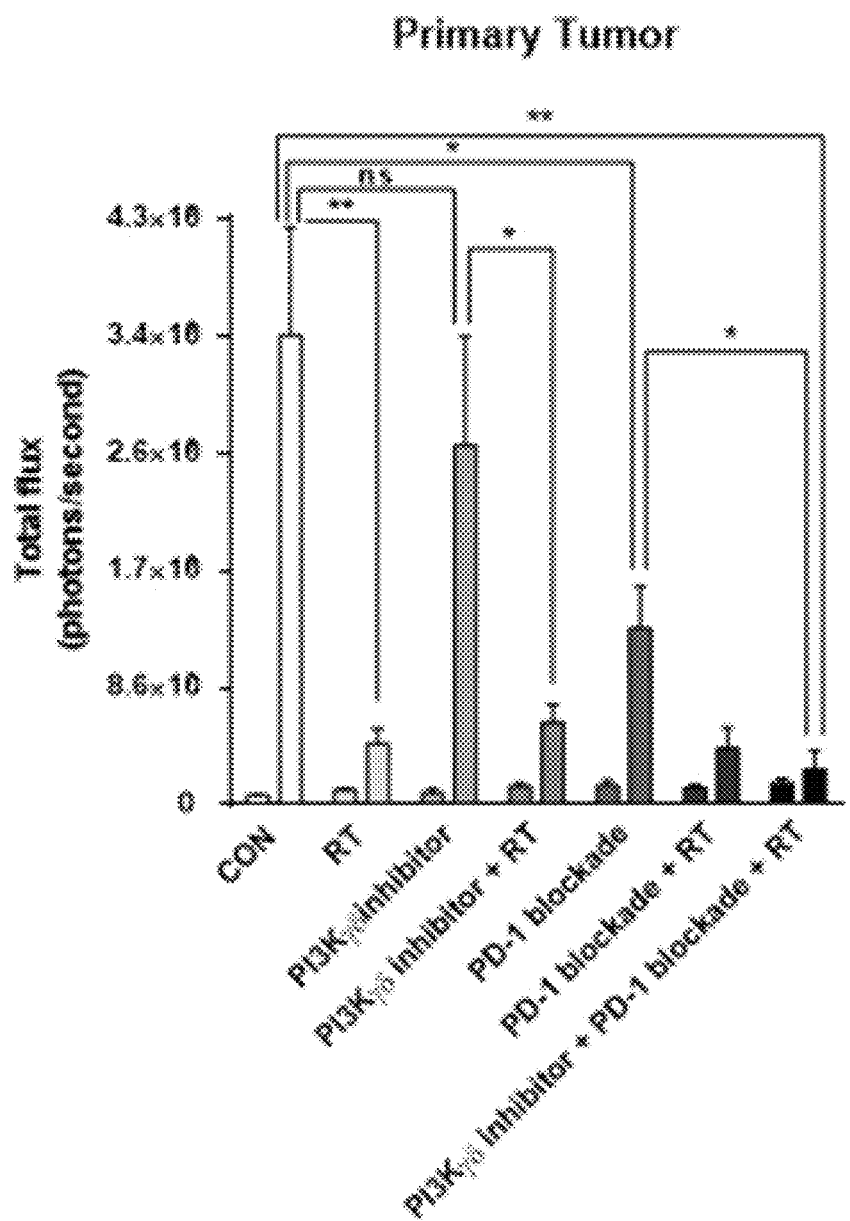

[FIG. 6c]
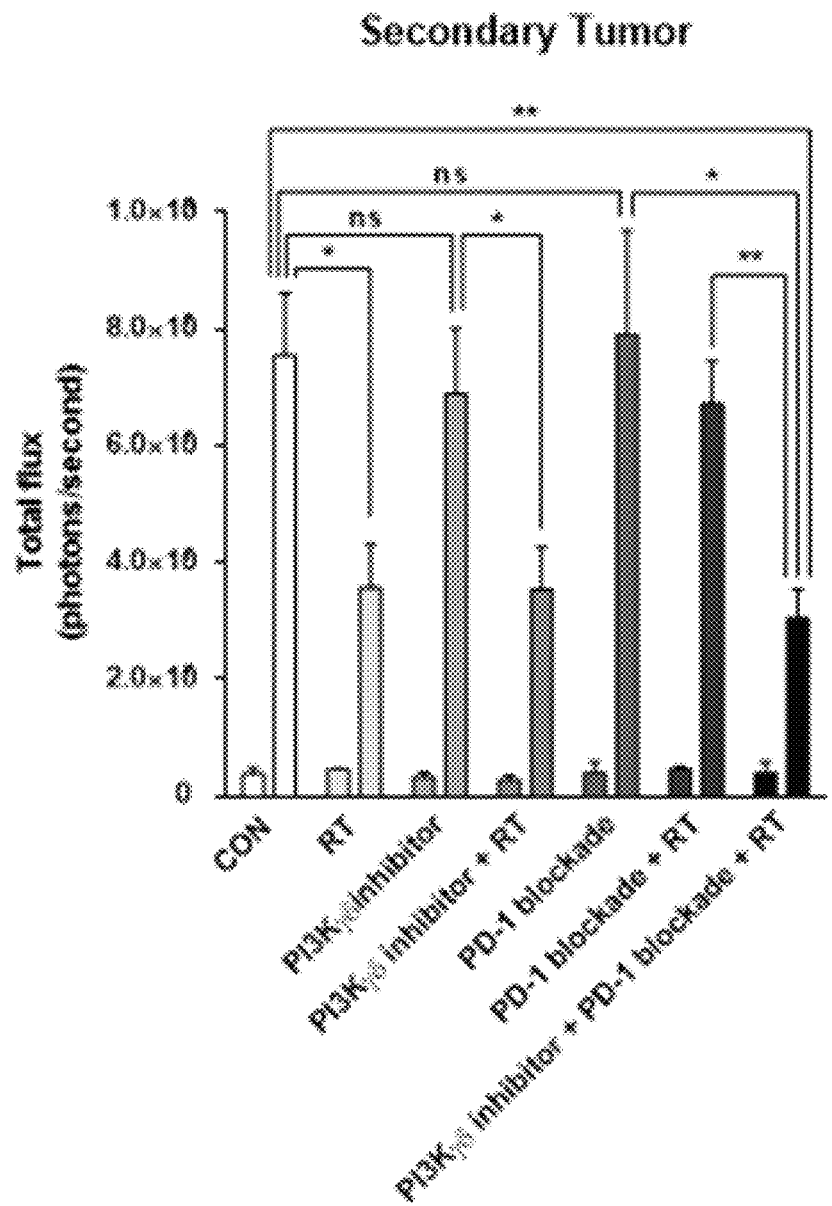

[FIG. 7a]
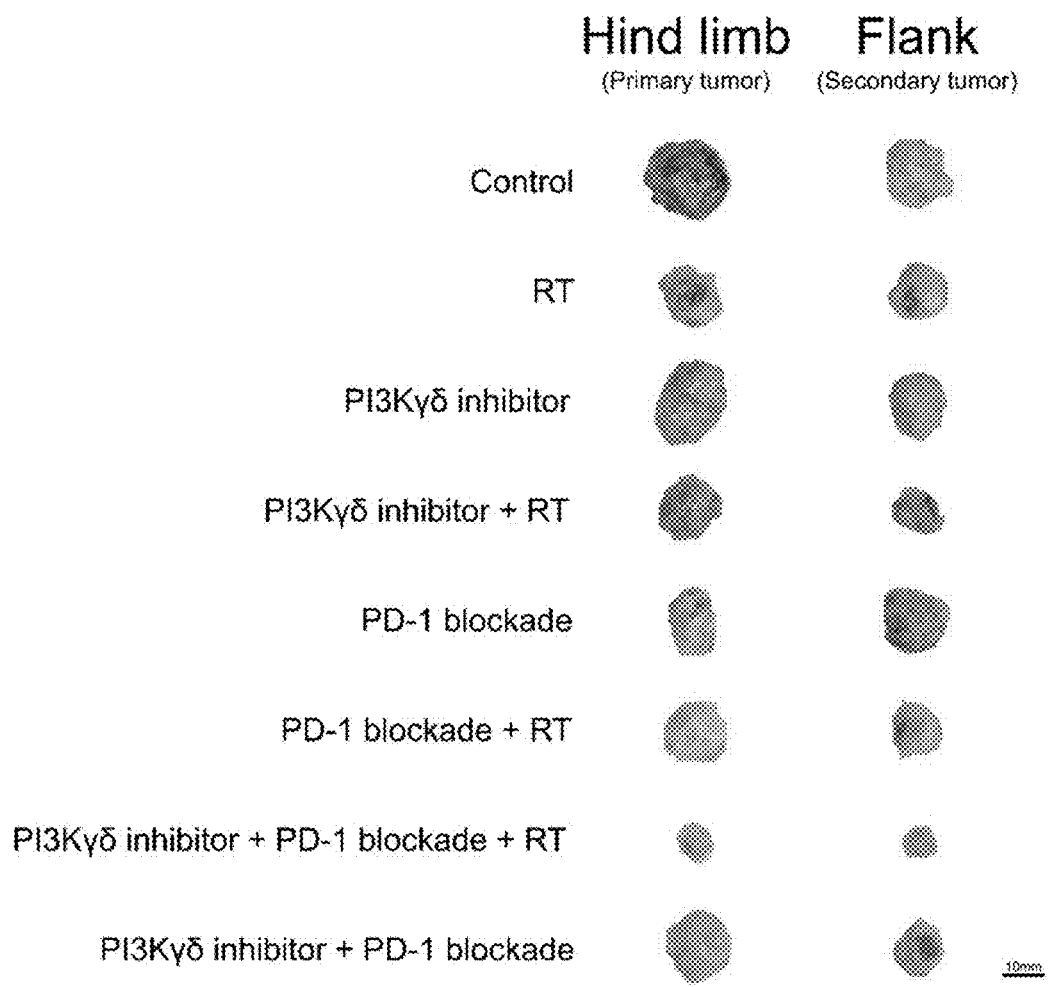

[FIG. 7b]
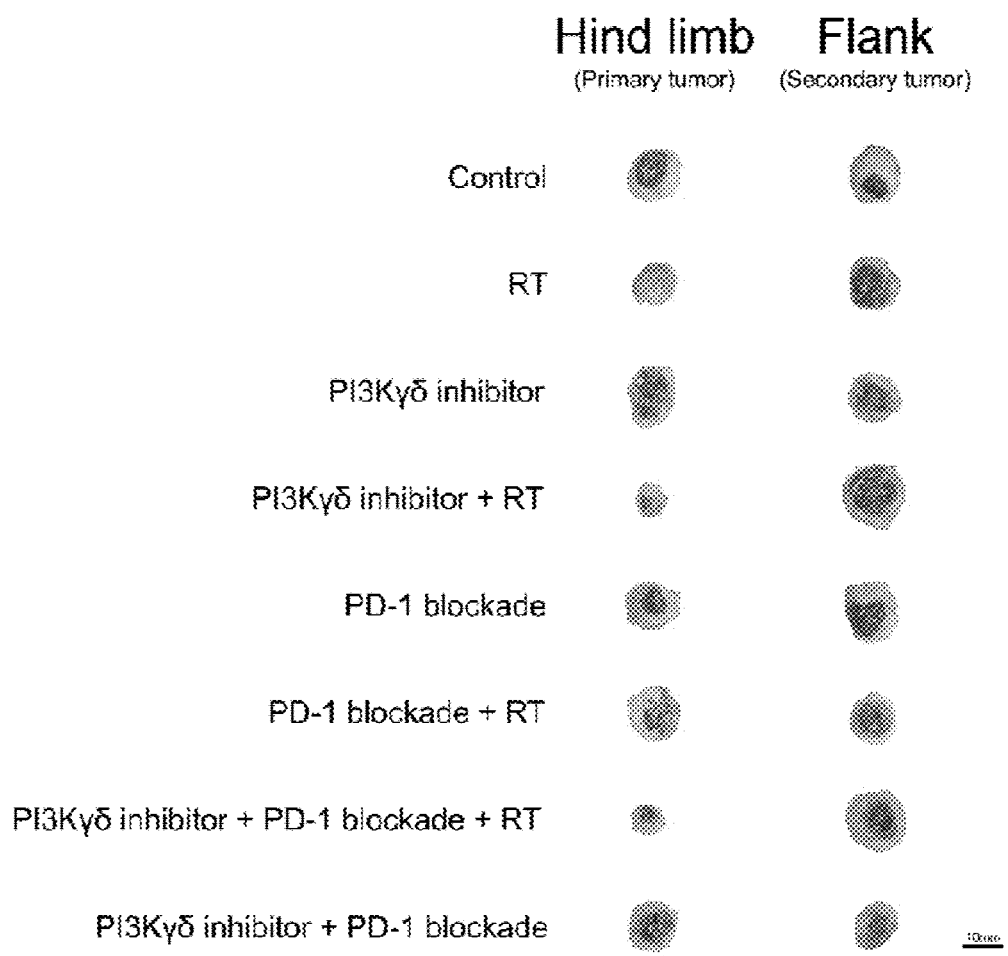

METHOD OF TREATING METASTATIC TRIPLE NEGATIVE BREAST CANCER WITH RADIOTHERAPY COMBINED WITH PHOSPHATIDYL INOSITOL-3 KINASE DELTA/GAMMA INHIBITORS AND ANTI-PD-1 ANTIBODIES

TECHNICAL FIELD

The present invention relates to an effective combined therapy for triple negative breast cancer, and more specifically, it relates to a pharmaceutical composition to be administered with radiotherapy, comprising a phosphatidylinositol 3-kinase (hereinafter, referred to as "PI3K") inhibitor and a programmed cell death protein 1 (hereinafter, referred to as "PD-1) blockade, and a method of treatment of triple negative breast cancer.

BACKGROUND ART

Breast cancer has been known as a cancer that shows clinically and pathologically very complicated, and yet diverse cases. Recently, various target therapeutic agents that have shown to be effective in treating breast cancer have been developed. Thus, breast cancer is also gradually classified according to the expression of therapeutic targets.

Therapeutic targets for breast cancer well-known so far are hormone receptors and HER2 overexpression, and treating these targets has enhanced breast cancer prognosis. Recently, breast cancer has been evaluated at a genomic level by studying its gene expression. Breast cancer can be classified by DNA microarray into luminal A group (estrogen receptor positive, HER2 negative), luminal B group (estrogen receptor positive, HER2 positive), HER2 overexpression group (estrogen receptor negative, HER2 positive), basal-like group which is estrogen receptor and HER2 negative, and normal group. In particular, the basal-like breast cancer is a group that generally has no hormone receptor and does not express HER2/neu and has been known to have lots of early relapse than other groups and have poor prognosis. However, such classification at a genomic level is difficult to be clinically applied, and therefore a method of classifying breast cancer by expression of hormone receptors and HER2 by immunohistochemical staining is currently more prevalently used.

Triple negative breast cancer is breast cancer in which expression of estrogen receptors (ER), progesterone receptors (PR) and HER2 are all negative in immunohistochemical staining, and accounts for approximately 10-15% of all breast cancers. Triple negative breast cancer is not completely identical to the basal-like breast cancer, but their clinical manifestations are very similar, and therefore they are dealt similarly in actual clinical setting. Triple negative breast cancer patients have been known to show relatively poor prognosis compared to non-triple negative breast cancer patients. Accordingly, it is imperative to develop a therapeutic agent for triple negative breast cancer.

Breast cancer is classified immunologically into "cold" tumor in that it has few CD8+ cells and has low tumor mutation burden. Only 20% of breast cancer has been known as PD-L1 positive tumor. However, the tumor microenvironment of triple negative breast cancer (TNBC) is quite different from general breast cancer, as TNBC is characterized as immunogenic tumor with relatively high number of tumor infiltrated lymphocytes and high PD-L1 expression. Such characteristics of triple negative breast cancer suggest that triple negative breast cancer may show good responses to immune checkpoint blockades, but it has been reported that the response rate of the immune checkpoint blockade treatment alone in the treatment of triple negative breast cancer is merely 5 to 19% in the conventional clinical trials.

Such low response rate may be due to adaptive resistance to immunotherapy. The regulatory T cells ($T_{regs}$ or $T_{reg}$), myeloid-derived suppressor cells (MDSCs), and/or M2 tumor-associated macrophages (TAMs) present in the tumor microenvironment have been known to play important roles in adaptive resistance to immunotherapy to reduce the effect of immunotherapy.

Meanwhile, a successful case of immune checkpoint blockade treatment in progressive and metastatic cancer has been recently reported. The method of combining radiotherapy with the use of immune checkpoint blockade has received a great attention, and many clinical trials related thereto are in progress.

In particular, radiotherapy is predicted to have an immunogenic effect, and the major mechanism of the immunogenic effect is described as immunogenic cell death which secretes danger-associated molecular patterns (DAMPs) such as high mobility group box 1 (HMGB1). Specifically, DAMPs secreted by immunogenic cell death collect and activate antigen-presenting cells and induce priming of cytotoxic T cells. Pro-immunogenic responses by radiotherapy convert the irradiated tumor into in situ vaccines, which in turn contribute to local regulation of tumor and prevention of distant metastasis. This is also shown to play a role of intensifying immunoreactions of hosts required for responses to the immune checkpoint inhibitor and helping to recover tumor with originally poor immune activity.

On the other hand, the PI3K-AKT-mTOR pathway has been known to play an important function in cell survival, growth and differentiation. PI3K family is classified into 3 classes (I to III), and Class I PI3K is a heterodimer and consists of one catalytic subunit (p110α, β, γ, δ) and one regulatory subunit (p85). PI3Kδ which is a major isotope activated by T cell receptors is a therapeutic target mainly in blood cancer, and has been reported to show an immunosuppressing effect by regulating regulatory T cells.

At first, PI3Kγ has been known as one of cell modification mechanisms which generates tumor by overexpression of p110γ, and recently, it has been reported that PI3Kγ acts on macrophages in the tumor microenvironment and involves in the reduction of anti-tumor immune functions. It has been reported that promotion of secretion of various immunosuppressing cytokines, including increasing expression of immune checkpoints such as PD-L1 (Programmed death-ligand 1) involves in the reduction of anti-tumor immune functions. However, no studies or clinical trials in animal models or patients with breast cancer have been reported to date.

In case of PI3Kδ, it has been also reported that, the regulation and survival of tumor in mice in which p110δ is inactivated have increased as the function of regulatory T cells is inhibited and some polymorphonuclear myeloid-derived suppressor cells (polymorphonuclear MDSCs) are inhibited.

DISCLOSURE

Technical Problem

The present inventors have studied the effectiveness of a combination therapy relative to a single therapy of an immune checkpoint inhibitor in intensifying immune reactions of a host and in preventing adaptive resistance by controlling immune suppressor cells. As a result, they have confirmed that a triple combination therapy of a PI3Kγ δ inhibitor and a PD-1 blockade with radiotherapy (RT) had a synergistic anti-cancer effect in the treatment of a triple negative breast cancer animal model.

A purpose of the present invention is to provide a pharmaceutical composition comprising a PI3K inhibitor and a PD-1 blockade to be combined with radiotherapy, for treatment of triple negative breast cancer.

Another purpose of the present invention is to provide a method of treatment of triple negative breast cancer, comprising administering a PI3K inhibitor; administering a PD-1 blockade; and performing radiotherapy.

Technical Solution

The present invention relates to a pharmaceutical composition for alleviating or treating triple negative breast cancer, to be combined with radiotherapy, comprising a PI3K inhibitor and a PD-1 blockade, and a method of treatment of triple negative breast cancer using the same.

Hereinafter, the present invention will be described in more detail.

The pharmaceutical composition for alleviating or treating of triple negative breast cancer provided by the present invention is combined with radiotherapy and comprises a PI3K inhibitor and a PD-1 blockade.

Herein, "triple negative breast cancer" is breast cancer in which expressions of estrogen receptors (ER), progesterone receptors (PR) and HER2 are all negative in immunohistochemical staining, and may include or be used in combination with basal-like breast cancer (BLBC).

Herein, "PI3K inhibitor" means an inhibitor against PI3Kγ and/or PI3Kδ unless special circumstances exist.

As for the PI3K inhibitor, any inhibitor against PI3K γ and/or PI3K δ may be used without limitation, and for example, the PI3K inhibitor may be one or more, two or more, or all 3 kinds selected from the group consisting of duvelisib, tenalisib, and idelalisib, but not limited thereto.

For the pharmaceutical composition for alleviating or treating triple negative breast cancer provided by the present invention, the PI3K inhibitor may suppress regulatory T cells ($T_{regs}$ or $T_{reg}$) and/or myeloid-derived suppressor cells (MDSCs) and/or M2 tumor-associated macrophages (TAMs) which involve in adaptive resistance in tumor. Accordingly, by comprising a PI3K inhibitor, the present invention can reduce adaptive immune resistance in the tumor microenvironment to enhance the effect of immunotherapy compared to cases in which a PD-1 blockade or radiotherapy is used alone, or a PD-1 blockade and radiotherapy are used in combination.

For the pharmaceutical composition for alleviating or treating triple negative breast cancer provided by the present invention, any PD-1 blockade known in the art may be used without limitation, and for example, it may be one or more selected from the group consisting of pembrolizumab, and nivolumab, or a combination of the two kinds.

The PD-1 blockade functions as an immunotherapeutic agent against immunogenic malignant tumor, for example, triple negative breast cancer (TNBC). When only a conventional immune checkpoint inhibitor is treated to triple negative breast cancer, the reaction rate has been very low. However, when the pharmaceutical composition of the present invention is combined with radiotherapy, there is an advantage of significantly lowering the rate of increase in the tumor volume than single treatment of the PD-1 blockade.

In one embodiment, the tumor volume in the TBNC allograft animal model treated by triple combination of the PI3K inhibitor, PD-1 blockade and radiotherapy was 0.16 times compared to the no-treatment control group, 0.26 times compared to the PD-1 blockade single treatment group, 0.22 times compared to the PI3K inhibitor single treatment group, 0.29 times compared to the radiotherapy single treatment group, 0.36 times compared to the PI3K inhibitor and radiotherapy combination treatment group, and/or 0.61 times compared to the combination of the PD-1 blockade and radiotherapy. Accordingly, it was confirmed that it had a significantly excellent tumor growth inhibitory effect compared to the conventional anti-cancer treatment method.

In the pharmaceutical composition provided by the present invention, the PD-1 blockade and PI3K inhibitor may be administered simultaneously in a mixture or sequentially, in a mass ratio and/or a volume ratio of 1:9 to 9:1 (PD-1 blockade:PI3K inhibitor, hereinafter, same), a mass ratio and/or a volume ratio of 1:5 to 5:1, or a mass ratio and/or a volume ratio of 2:5 to 5:2, into a subject. In one embodiment, the concentration of each inhibitor is in a range commonly applied and acceptable for research and/or treatment, and it may be extrapolated into an acceptable lethal dosage range of the drug.

In other one embodiment, the PD-1 blockade and PI3K inhibitor in the pharmaceutical composition provided by the present invention may be administered in a mixture or sequentially regardless of the order, in a mass ratio of 1:1 to 10:1 (PD-1 blockade:PI3K inhibitor, hereinafter, same), a mass ratio of 1:1 to 5:1, or a mass ratio of 1:1 to 5:2, into a subject.

The content of the PD-1 blockade and PI3K inhibitor in the pharmaceutical composition provided by the present invention may be 0.1 to 10% by weight, 0.1 to 5% by weight, or 0.1 to 1% by weight in the total pharmaceutical composition, but not limited thereto.

The pharmaceutical composition provided by the present invention may be administered at an appropriate interval, in consideration of patient's age, clinical stage, body weight, prognosis and/or other matters commonly considered in the art during administration. For example, it may be administered once to 35 times per week, once to 21 times per week, once to 14 times per week, once to 7 times per week, once to 5 times per week, once to 3 times per week, once to twice per 2 days, or combinations thereof.

The pharmaceutical composition provided by the present invention may be combined with radiotherapy (RT) for treatment of triple negative breast cancer.

For radiotherapy, all radiotherapy methods known in the art may be used, and in one embodiment, for radiation capacity per time, the radiotherapy known to increase the possibility of activating the immune system may be used. For example, as a range of radiotherapy enforceable for actual research or treatment, it may be performed at a dose of 8 to 12 Gy in 1 to 5 fractions (Fx), at an irradiation interval of 1 to 3 days or 2 to 3 days.

The pharmaceutical composition of the present invention comprising a PI3K inhibitor and a PD-1 blockade is combined with radiotherapy and has an effect of increasing an immunotherapeutic effect of immunogenic tumor. Specifically, the tumor tissue in which the pharmaceutical composition for alleviating or treating triple negative breast cancer provided by the present invention is treated may have one or more, two or more, three or more selected from the group consisting of the following listed characteristics, or all the following characteristics:

(1) reduction of the growth rate of tumor tissue;
(2) reduction of the ratio of $T_{reg}$ cells in tumor tissue;
(3) reduction of the ratio of MDSC cells in tumor tissue;
(4) increase of the ratio of CD8 positive T cells in tumor tissue; and
(5) reduction of the ratio of M2 TAM cells and/or increase of the ratio of M1 TAM compared to M2 TAM in tumor tissue.

The pharmaceutical composition for alleviating or treating triple negative breast cancer provided by the present invention inhibits growth of tumor or reduces the growth rate of tumor. In one embodiment, the tumor size (volume) in a subject in which the pharmaceutical composition for alleviating or treating triple negative breast cancer provided by the present invention is administered may be 0.25 times or less, 0.2 times or less or 0.18 times or less, compared to the no-treatment control group, but not limited thereto. In one embodiment, the tumor size in a subject in which the pharmaceutical composition for alleviating or treating triple negative breast cancer provided by the present invention is administered may be 0.5 times or less, 0.4 times or less, or 0.3 times or less compared to the radiotherapy single treatment group, and may be 0.5 times or less, 0.4 times or less, 0.3 times or less, or 0.25 times less, compared to the PI3K inhibitor single treatment group, and may be 0.5 times or less, 0.4 times or less, or 0.3 times or less, compared to the PD-1 blockade single treatment group, but not limited thereto.

In other one embodiment, the tumor size in a subject in which the pharmaceutical composition for alleviating or treating triple negative breast cancer provided by the present invention is administered may be 0.8 times or less, 0.7 times or less, 0.6 times or less, 0.5 times or less, or 0.4 times or less, compared to the radiotherapy and PI3K inhibitor combination treatment group, and may be 0.8 times or less, 0.7 times or less, or 0.65 times or less, compared to the radiotherapy and PD-1 blockade combination treatment group, but not limited thereto.

The pharmaceutical composition for alleviating or treating triple negative breast cancer provided by the present invention reduces the ratio of $T_{reg}$ cells in tumor tissue.

The $T_{reg}$ cells are immunoregulatory T cells, and have been known to play an important role in adaptive resistance during immunotherapy, and reduce the effect of immunotherapy. Accordingly, the pharmaceutical composition provided by the present invention may inhibit adaptive resistance and enhance the effect of immunotherapy by reducing the ratio of $T_{reg}$ cells. In one embodiment, the $T_{reg}$ cell ratio in tumor tissue treated with a combination of the pharmaceutical composition of the present invention with radiotherapy (triple combination) may be at a level of 60% or less, 50% or less, 40% or less, 35% or less, 10 to 60%, 10 to 50%, 10 to 40%, 10 to 35%, 20 to 60%, 20 to 50%, 20 to 40%, or 20 to 35%, but not limited thereto.

In one example, when the PI3K inhibitor and PD-1 blockade were combined with radiotherapy (triple combination), the $T_{reg}$ cell ratio was shown at a level of 33.7% compared to the no-treatment control group, 37% compared to the combination of the PD-1 blockade and radiotherapy, and about 59.4% compared to the PI3K inhibitor and radiotherapy combination treatment.

The pharmaceutical composition for alleviating or treating triple negative breast cancer provided by the present invention reduces the ratio of MDSC cells in tumor tissue.

MDSC is a myeloid-derived immunosuppressing cell, and has been known to play an important role in adaptive resistance during immunotherapy and reduce the effect of immunotherapy. Accordingly, the pharmaceutical composition provided by the present invention may suppress adaptive resistance of tumor and enhance the effect of immunotherapy by reducing the ratio of MDSC cells. In one embodiment, the ratio of MDSC cells in tumor tissue treated with a combination of pharmaceutical composition of the present invention and radiotherapy (triple combination) may be at a level of 90% or less, 80% or less, 75% or less, 10 to 90%, 10 to 80%, 10 to 75%, 20 to 95%, 20 to 80%, 20 to 75%, 50 to 90%, 50 to 80%, or 50 to 75%, compared to the no-treatment control group, but not limited thereto.

In one example, when the PI3K inhibitor and PD-1 blockade were combined with radiotherapy (triple combination), the MDSC cell ratio was shown to be at a level of 73.4% compared to the no-treatment control group, at about 70.2% compared to the combination of PD-1 blockade and radiotherapy, and at about 88.6% compared to the PI3K inhibitor and radiotherapy.

The pharmaceutical composition for alleviating or treating triple negative breast cancer provided by the present invention increases the ratio of CD8 positive T cells in tumor tissue.

A CD8 positive T cell has been also known as a killer T cell, or a cytotoxic T cell, and has been known to destroy tumor cells. Accordingly, the pharmaceutical composition provided by the present invention may inhibit tumor growth of triple negative breast cancer by increasing the ratio of CD8 positive T cell in tumor. In one embodiment, the CD8 positive T cell ratio in tumor tissue in which the pharmaceutical composition of the present invention is combined with radiotherapy (triple combination) may be 2 to 100 times, 2 to 50 times, 2 to 30 times, 2 to 20 times, 5 to 100 times, 5 to 50 times, 5 to 30 times, 5 to 20 times, 10 to 100 times, 10 to 50 times, 10 to 30 times or 10 to 20 times, compared to the no-treatment control group, but not limited thereto.

In one example, when the PI3K inhibitor and PD-1 blockade were combined with radiotherapy (triple combination), the CD8 positive T cell ratio was about 16.6 times compared to the no-treatment control group, about 2.24 times compared to the combination of the PD-1 blockade and radiotherapy, and about 2.42 times compared to the combination of PI3K inhibitor and radiotherapy.

The pharmaceutical composition for alleviating or treating triple negative breast cancer provided by the present invention reduces the ratio of M2 TAM cells in tumor tissue.

M2 TAM cell is an M2 tumor-associated macrophage, and has been known to involve in an anti-inflammatory reaction and a remodeling of a tissue. More specifically, M2 TAM is the most important component cell among immunocytes infiltrated to cancer, and has been known to play an important role in formation of cancer and the inflammatory environment, and inducement tumor growth. Further, it is also involved in cancer angiogenesis, infiltration and metastasis, and in the suppression of anti-cancer immunity. Therefore, it has become a target of cancer immunotherapy. Accordingly, it can be confirmed that the pharmaceutical composition provided by the present invention has an excellent anti-cancer effect by reducing the ratio of M2 TAM in tumor tissue.

In one embodiment, the ratio of M2 TAM in tumor tissue in which the pharmaceutical composition of the present invention is combined with radiotherapy (triple combination), may be 50% or less, 40% or less, 35% or less, 10 to 50%, 10 to 40%, 10 to 35%, 20 to 50%, 20 to 40%, 20 to 35%, 30 to 50%, 30 to 40%, or 30 to 35%, compared to the no-treatment control group, but not limited thereto.

In one example, the M2 TAM cell ratio in the no-treatment control group was at a level of 4.68%, but it was shown at a level of 1.50% in mice treated with a combination of PI3K inhibitor/PD-1 blockade administration and radiotherapy (triple combination). The ratio was lower than the M2 TAM ratio of radiotherapy only (5.22%) or the M2 TAM ratio of PI3K inhibitor administration (2.43%), indicating that the triple combination treatment showed the biggest width of decrease, and therefore it was confirmed that triple combination had an excellent anti-cancer effect.

The pharmaceutical composition for alleviating or treating triple negative breast cancer provided by the present invention may increase the ratio of M1 TAM cell compared to M2 TAM cell in tumor tissue.

M2 TAM cell has been known to involve in formation of cancer and M1 TAM cell has been known to involve in anti-cancer activity, as aforementioned, and therefore it may be predicted to have an excellent anti-cancer activity as the ratio of M1 TAM cell is increased.

In one embodiment, the ratio of M1 TAM in tumor tissue in which the pharmaceutical composition of the present invention is combined with radiotherapy, may be 1.1 to 3 times, 1.1 to 2.5 times, 1.1 to 2 times, 1.3 to 3 times, 1.3 to 2.5 times, 1.3 to 2 times, 1.5 to 3 times, 1.5 to 2.5 times, or 1.5 to 2 times, compared to the no-treatment control group, but not limited thereto.

In one example, the M1 TAM cell ratio in the no-treatment control group was at a level of 30.27%, but it was shown at a level of 53.92% in mice in which administration of the PI3K inhibitor and PD-1 blockade and radiotherapy were combined (triple combination). Thus, it was confirmed that the anti-cancer activity by M1 TAM was significantly increased by triple combination, compared to the PD-1 blockade single administration (26.13% level) and/or dual combination of the PI3K inhibitor and radiotherapy (27.18% level). In addition, in triple combination, a higher value of M1 TAM ratio was shown than the PI3K inhibitor single administration (40.98%) showing the biggest width of increase of M1 TAM ratio among other experimental groups. Accordingly, it was confirmed that the anti-cancer effect was significantly increased in triple combination.

The pharmaceutical composition provided by the present invention may inhibit growth of metastatic tumor and/or recurrent tumor occurring on the site other than the primary site of triple negative breast cancer (TNBC). In one embodiment, the combination of the PI3K inhibitor and PD-1 blockade with radiotherapy (triple combination) may show a similar change pattern to the change of the ratio of $T_{reg}$, MDSC, and/or CD8+ T cell.

In one example, in the spleen and tumor draining lymph nodes of the mouse model treated by triple combination, the $T_{reg}$ and MDSC ratios were reduced compared to the control group, and the ratio of $CD8^+$ T cell was increased, and thereby it was confirmed that the immunotherapeutic effect was shown for other sites other than the primary site in a subject to be administered.

Accordingly, the pharmaceutical composition provided by the present invention, when combined with radiotherapy, may be used for alleviating and/or treating triple negative breast cancer (primary tumor) and its metastatic tumor and/or recurrent tumor.

Herein, the "metastatic tumor" means tumor occurred by triple negative breast cancer is transferred to other places different from the occurring location (primary site). The "recurrent tumor" means the same kind of tumor as the primary tumor, occurred at the same location as the primary tumor and/or the location isolated in distance.

The administration method of the pharmaceutical composition provided by the present invention is not particularly limited, and for example, it may be administered by one or more, two or more, or three or more of administration methods selected from the group consisting of for oral administration, intravenous injection, intramuscular injection, intradural injection, subcutaneous injection, sublingual administration, buccal mucosa administration, intrarectal administration, vaginal administration, ocular administration, ear administration, intranasal administration, inhalation administration, spray administration, skin administration and dermal administration. In one embodiment, the pharmaceutical composition may be administered by injection.

The formation of the pharmaceutical composition provided by the present invention may be prepared by selecting an appropriate method for treating triple negative breast cancer, and for example, it may be in the forms of dried syrup, oral disintegrating tablet, buccal tablet, foaming tablet, powder, sublingual tablet, liquid, tablet, capsule, chewable tablet, mouth wash, enema, nasal spray, ointment, cream, lotion, nasal drop, eye drop, ear drop, vaginal suppository, patch, rectal suppository, inhalant (aerosol), inhalant or a combination thereof, but not limited thereto, and an appropriate formation may be selected and used in consideration of body weight, age, stage and/or prognosis of a subject.

The pharmaceutical composition provided by the present invention may further comprise an additive for the purpose of increasing pharmaceutical usefulness, facilitating formulation, promoting stabilization of formulations, and improving appearance, and the like. As an additive, if necessary, an excipient, stabilizer, preservative, buffer, sweetening agent, suspension, emulsifier, aromatic agent, solubilizer, coloring agent, concentrate, or combinations thereof may be used. The additive does not show a direct pharmacological action on the pharmaceutical composition of the present invention, and it may be freely selected and used in a range which does not change the therapeutic effect of the pharmaceutical composition of the present invention or does not cause inconvenience for tests.

In one embodiment, when the pharmaceutical composition of the present invention is provided in a form of injection, the additive may comprise one or more, two or more, three or more, selected from the group consisting of a solvent, solubilizer, buffer, isotonic agent, stabilizer, antioxidant, analgesic, and suspension. The content and/or kind of the additive may be freely selected and used in a range known in the art by those skilled, within the scope of the present invention.

Another embodiment of the present invention relates to a method of treatment of triple negative breast cancer, comprising administering a PI3K inhibitor; administering a PD-1 blockade; and performing radiotherapy. The method may further comprise confirming a triple negative breast cancer patient or a subject requiring treatment of triple negative breast cancer, before the administering the PI3K inhibitor and PD-1 blockade and performing radiotherapy. The subject may be a mammal such as a human, or a cell derived therefrom (for example, cancer cell). The disclosed methods can induce and/or promote abscopal effect.

The contents about the PI3K inhibitor, PD-1 blockade, and radiotherapy are as described above. In case of a triple combination of the PI3K inhibitor, PD-1 blockade, and radiotherapy, there is an effect of reducing adaptive immune resistance in the triple negative breast cancer environment compared to a single or dual combination of each treatment to enhance the effects of immunotherapy and increase the anti-cancer activity.

The administration of the PI3K inhibitor and/or PD-1 blockade may be conducted simultaneously or at a delayed time, and the administration method and/or dose are substantially same as the administration method of the pharmaceutical composition, and the administration method and/or dose may be freely selected within the therapeutic range of triple negative breast cancer as occasion demands.

The radiotherapy may be performed simultaneously or at a delayed time with administration of the PD-1 blockade and PI3K inhibitor, and in one embodiment, the radiotherapy and administration of the inhibitor may be conducted on the same day or different days. In one embodiment, when the radiotherapy and administration of the inhibitor are conducted on the same day, the inhibitor may be administered after an appropriate time required for recovery in consideration of the health condition of the patient after radiotherapy, but not limited thereto.

Advantageous Effects

The method of treatment of triple negative breast cancer and the pharmaceutical composition provided by the present invention are administered combined with radiotherapy to enhance anti-cancer (anti-tumor) effects and improve a low reaction rate due to adaptive immune resistance of tumor which occurs during immunotherapy or radiotherapy of immunogenic tumor, for example, triple negative breast cancer.

BRIEF DESCRIPTION OF THE DRAWINGS

FIG. 1a is a graph showing the volume change of tumor according to each treatment method in the triple negative breast cancer allograft mouse model.

FIG. 1b is a graph showing the survival rate according to each treatment method in the triple negative breast cancer allograft mouse model.

FIG. 2a to FIG. 2c are graphs showing the FACS analysis result for spleen tissue, and the ratios of the regulatory T cells (FIG. 2a); polymorphonuclear myeloid-derived suppressor cells (PMN-MDSC, FIG. 2b); and CD8 positive T cells (FIG. 2c), analyzed from the FACS result.

FIG. 3a to FIG. 3c are graphs showing the FACS analysis results for tumor draining lymph nodes, and the ratios of the regulatory T cells (FIG. 3a), myeloid-derived suppressor cells (PMN-MDSC, FIG. 3b); and CD8 positive T cells (FIG. 3c), analyzed from the FACS results.

FIG. 4a to FIG. 4c are graphs showing the FACS analysis results for tumor microenvironment (tumor tissue), and the ratios of the regulatory T cells (FIG. 4a); myeloid-derived suppressor cells (PMN-MDSC and M-MDSC, FIG. 4b); and CD8 positive T cells (FIG. 4c), analyzed from the FACS results.

FIG. 5 is the FACS analysis results for tumor microenvironment (tumor tissue) and the result of performing M1 or M2 TAMs therefrom.

FIG. 6a to FIG. 6c are showing the imaging result (FIG. 6a); a luminescence graph for primary tumor (FIG. 6b); and a luminescence graph for secondary tumor (FIG. 6c).

FIG. 7a to FIG. 7b are showing the macroscopic images of primary and secondary tumor of mouse model (FIG. 7a) and nude mouse model (FIG. 7b).

DETAILED DESCRIPTION OF THE EMBODIMENTS

Hereinafter, the contents of the present invention will be described in more detail by examples. However, the scope of the present invention is not limited by the following examples.

Example 1. Cell Culture and Preparation of Allograft Mouse Model 1-1. Culture of Breast Cancer Cell Line A triple negative breast cancer cell line (4T1-luc) was cultured in DMEM (Dulbecco's Modified Eagle's Medium, CORNING™) medium containing 10% (v/v) fetal bovine serum (FBS) and 1% (w/v) Penicillin-Streptomycin, using a cell culture flask, in a thermostat cell culture device under the condition of 37° C., 5% $CO_2$.

1-2. Preparation of Allograft Mouse Model $6 \times 10^5$ 4T1-luc triple negative breast cancer cells prepared in Example 1-1 were injected to the right hindlimb of a BALB/c female age standard (8 weeks) mice. At the 10th day after injecting each of the cancer cells, the mice with the tumor volume up to 40 $mm^3$ were selected, and were used for later experiments.

Example 2. Measurement of Size Change of Tumor and Survival Rate According to Treatment Methods 2-1. Measurement of Size Change of Tumor The triple negative breast cancer (TNBC) mouse model prepared by the method of Example 1-2 was assigned to 7 groups in total from the 10th day after cancer cell transplantation, and each treatment method was performed, and it was grouped into 7 groups so that the tumor mean volume of 7 mice was 40 $mm^3$ per group, and were used for later experiments.

The 7 groups were composed of control group (no-treatment group), radiotherapy group, PI3Kγ δ inhibitor (duvelisib) treatment group, combined treatment group of PI3Kγ δ inhibitor and radiotherapy, PD-1 blockade treatment group, combined treatment group of PD-1 blockade and radiotherapy, and triple combined treatment group of PI3Kγ δ inhibitor, PD-1 blockade and radiotherapy, respectively. Each treatment was progressed for 31 days after tumor transplantation.

The radiotherapy used electron beam, and 24 Gy in total was irradiated in 3 fractions, once per 2 days or 3 days (Monday, Wednesday and Friday), for 1 week (8 Gy×3). The PD-1 blockade and the PI3Kγ δ inhibitor (duvelisib) were administered by injection at doses of 10 mg/kg and 4 mg/kg, respectively, 6 times in total, once per 2 days or 3 days (Monday, Wednesday and Friday), over 2 weeks in total. On the day where the radiotherapy and drug administration overlapped, the drug was administered after confirming that the mice recovered from anesthesia in 4 hours after radiotherapy.

On the day of each treatment, the size of tumor, the length and width were measured using Vernier caliper, and then the volume ($mm^3$) of tumor was calculated by the method of the following equation 1.

$$\text{Volume (mm}^3\text{)} = \text{length (mm)} \times \text{width (mm)}^2 \times 0.5 \quad \text{[Equation 1]}$$

FIG. 1a showed the graph of the tumor volume change over time according to each treatment method, and the following Table 1 showed the mean value of the tumor volume of each treatment group at the 31$^{st}$ day of the experiment.

TABLE 1

| Classification | Mean tumor volume (mm$^3$) |
| --- | --- |
| Control group (no-treatment) | 1383.08 |
| RT | 949.64 |
| PI3K γ δ inhibitor | 786.59 |
| PI3K γ δ inhibitor + RT | 311.05 |
| PD-1 blockade | 1107.81 |
| PD-1 blockade + RT | 483.15 |
| PI3K γ δ inhibitor + PD-1 blockade + RT | 143.30 |

As could be confirmed in the Table 1 and FIG. 1, the excellent inhibitory effect of tumor growth was confirmed compared to dual combined therapy, as the tumor volume was about 143.30 mm$^3$ in case of the triple combined therapy of the PI3Kγ δ inhibitor, PD-1 blockade and RT inhibitor. More specifically, this final tumor volume was just a size of 0.10 times compared to the control group, 0.15 times compared to the single treatment of radiotherapy, 0.18 times compared to the single treatment of the PI3Kγ δ inhibitor, 0.13 times compared to the PD-1 single treatment group, 0.46 times compared to the combination of the PI3Kγ δ inhibitor and radiotherapy, and 0.30 times compared to the combination of the PD-1 blockade and radiotherapy, and thus it was confirmed that the inhibitory effect of the pharmaceutical composition comprising the PD-1 blockade and PI3Kγ δ inhibitor combined with radiotherapy, provided by the present invention, was very excellent.

2-2. Survival Rate According to Treatment Methods

While performing the Example 2-1, the survival rate of each group was measured. For survival studies, mice were culled when tumors reached an average volume of 1000 mm$^3$ or they died.

FIG. 1B showed the graph of the survival rate over time according to each treatment method.

Over a period of more than 42 days, the survival rate was not decreased in case of the triple combined therapy of the PI3Kγ δ inhibitor, PD-1 blockade and RT inhibitor, and increase of the survival rate was statistically significant.

Example 3. Confirmation of Immunoregulatory Effect Using FACS

After completing the experiment of Example 2, tumor and spleen, and tumor draining lymph nodes were extracted from each mouse. For the tumor draining lymph nodes, inguinal lymph nodes which were the closest to the hindlimb calf site in which tumor was seeded were extracted. Then, each tissue was subject to single cell isolation, and thereafter, the immunoregulatory effect was confirmed using flow cytometric analysis (FACS).

More specifically, on the 31th day after tumor cell injection, each mouse was administered euthanasia, and then the spleen and tumor were extracted, respectively.

The tumor tissue was excised and subjected to fine chopping mechanical processing using a sterilized razor blade, and was treated with DNase 0.1 mg/ml and collagenase 1 mg/ml, respectively, and reacted at 36° C. for 30 minutes to obtain a single cell suspension.

The spleen tissue was excised and subjected to the mechanical processing by the same method as the tumor tissue, and then red blood cells were lysed by single cell suspension method (See Standard Recommended Sample Preparation Procedures of Thermofisher company) and the single cell isolation was completed.

After completing the single cell isolation from the tumor tissue and spleen tissue, to analyze infiltrated leukocytes, 1×10$^6$ cells per FACS tube were stained by FITC, PE, PerCP/Cy5.5, APC fluorescence, using CD3 antibody, CD8b antibody, Ly6G antibody, CD11b antibody, CD25 antibody, CD4 antibody, Ly6G antibody, CD25 antibody, Ly6C antibody, CD8a antibody, CD25 antibody, CD127 antibody and CD206 antibody, respectively.

Staining of each cell surface marker was conducted by reacting on ice for 30 minutes, and intracellular FOXP3 staining was progressed by the manual of eBioscience company.

For samples that finished each staining, using BD Bioscience FACSCALIBUR machines, fractions of regulatory T cells (T$_{regs}$ or T$_{reg}$), myeloid-derived suppressor cells (MDSCs), M1 or M2 tumor-associated macrophages (TAMs: M1 TAM or M2 TAM), and CD8$^+$ cytotoxic T cells, from the tumor microenvironment and spleen were calculated respectively. The analysis of FACS results used FLOWJO software, version 10, and the results are shown in FIG. 2a to FIG. 4c. Specifically, FIG. 2a to FIG. 2c represent the FACS analysis results in the spleen tissue, and FIG. 3a to FIG. 3c represent the FACS analysis results in the tumor draining lymph nodes, and FIG. 4a to FIG. 5 represent the FACS analysis results in the tumor tissue (tumor microenvironment).

The composition change of immunocytes in the draining lymph nodes and the spleen is a prerequisite for treatment to lead to adaptive resistance to inhibit tumor elsewhere. The change of immunocytes in the tumor draining lymph nodes (FIG. 3a to FIG. 3b) and spleen (FIG. 2a to FIG. 2b) confirmed in FIG. 2a to FIG. 4c, demonstrated that the combination of the pharmaceutical composition and radiotherapy provided by the present invention could go beyond the role of enhancing immunity in the tumor microenvironment of the simple primary anatomical location or antitumor inhibition of immunocytes, and generate adaptive resistance in order to have a function of suppressing tumor formation even for metastasis of other anatomical location other than the primary site or recurrent tumor.

The ratios of T$_{reg}$, MDSC(PMN_MDSC) and CD8+ T ells in the spleen and tumor draining lymph nodes and tumor tissue are shown in the following Tables 2 to 4.

TABLE 2

| | T$_{reg}$ ratio (%) | | |
| --- | --- | --- | --- |
| Classification | Spleen | Tumor draining lymph nodes | Tumor |
| Control group | 6.46 | 5.43 | 12.62 |
| RT | 16.77 | 7.36 | 16.23 |
| PI3K γ δ inhibitor | 2.93 | 2.33 | 3.63 |
| PI3K γ δ inhibitor + RT | 3.64 | 2.61 | 7.15 |
| PD-1 blockade | 5.85 | 5.69 | 8.27 |
| PD-1 blockade + RT | 15.95 | 6.46 | 11.51 |
| PI3K γ δ inhibitor + PD-1 blockade + RT | 2.69 | 1.89 | 4.25 |

TABLE 3

| Classification | PMN-MDSC ratio (%) | | |
|---|---|---|---|
| | Spleen | Tumor draining lymph nodes | Tumor |
| Control group | 58.70 | 3.63 | 26.55 |
| RT | 63.37 | 3.30 | 30.67 |
| PI3K γ δ inhibitor | 37.33 | 2.01 | 19.20 |
| PI3K γ δ inhibitor + RT | 36.75 | 2.77 | 21.98 |
| PD-1 blockade | 62.82 | 3.86 | 25.88 |
| PD-1 blockade + RT | 65.70 | 3.32 | 27.75 |
| PI3K γ δ inhibitor + PD-1 blockade + RT | 37.63 | 2.00 | 19.48 |

TABLE 4

| Classification | CD8$^+$ T cell ratio (%) | | |
|---|---|---|---|
| | Spleen | Tumor draining lymph nodes | Tumor |
| Control group | 13.87 | 15.93 | 1.64 |
| RT | 25.37 | 22.87 | 10.10 |
| PI3K γ δ inhibitor | 14.00 | 19.20 | 4.85 |
| PI3K γ δ inhibitor + RT | 22.02 | 22.33 | 11.23 |
| PD-1 blockade | 20.62 | 16.15 | 3.33 |
| PD-1 blockade + RT | 23.40 | 25.90 | 12.13 |
| PI3K γ δ inhibitor + PD-1 blockade + RT | 25.75 | 28.60 | 27.17 |

As could be confirmed in FIG. 5, when combining radiotherapy and the PD-1 blockade and PI3K inhibitor, the ratio of M1 TAM was the highest compared to radiotherapy or single or dual combination of each inhibitor, and the M1 TAM ratio compared to the control group (no-treatment group) increased about 1.8 times. M2 TAM showed about ⅓ of M2 TAM ratio in case of the triple combination compared to the control group, and showed the significantly low M2 TAM ratio compared to radiotherapy or single or dual combination of each inhibitor (Table 5).

TABLE 5

| Classification | M1 TAM ratio (%) | M2 TAM ratio (%) |
|---|---|---|
| Control group | 30.27 | 4.68 |
| RT | 35.72 | 5.22 |
| PI3K γ δ inhibitor | 40.98 | 2.43 |
| PI3K γ δ inhibitor + RT | 27.18 | 3.20 |
| PD-1 blockade | 26.13 | 4.49 |
| PD-1 blockade + RT | 31.27 | 6.75 |
| PI3K γ δ inhibitor + PD-1 blockade + RT | 53.92 | 1.50 |

M1 TAM inhibits tumor in the tumor microenvironment by secreting proinflammatory cytokines on the contrary to M2 TAM. Accordingly, as could be confirmed in the Table 5 and FIG. 5, it was confirmed that the immunotherapy efficiency of the pharmaceutical composition with the combined treatment of radiotherapy, comprising the PI3K inhibitor and PD-1 blockade of the present invention, in which M1 TAM widely increased and M2 TAM significantly decreased, was excellent.

Example 4. Confirmation of Increase in Abscopal Effect 4-1. Bioluminescence Imaging An animal model was prepared by injecting tumor cells to the right hindlimb in the same manner as in Example 1-2, and transplanting secondary tumor to the left flank. The animal model was grouped into 7 groups and treated in the same manner as Example 2-1. However, the radiotherapy was performed only for the right hindlimb.

Bioluminescence images were obtained using the IVIS Imaging System 100 series (Xenogen Corporation) according to the manufacturer's protocol. Mice were injected with luciferin (Promega, 2.5 mg/mouse) 10 min before imaging under anaesthesia (1-2% isoflurane). The acquired images included peak luminescence signals and were recorded for 10 min. To normalize initial minor differences in tumor burden, relative tumor burden was defined as (signal value at the time of last measurement−signal value at baseline)/(signal value at starting point). The calculated values for relative tumor burden were used in the statistical analysis.

The imaging results are shown in FIG. 6a to FIG. 6c.

The relative tumor burden in the secondary tumor confirmed in FIG. 6c demonstrated that the combination of the pharmaceutical composition and radiotherapy provided by the present invention could prevent or treat metastatic tumor or recurrent tumor by enhancing abscopal effect.

4-2. Size of Tumor after Treatment

After performing Example 4-1, tumor tissues were extracted from each group. The macroscopic images are shown in FIG. 7.

The group treated by triple combination of the PI3K inhibitor, PD-1 blockade and radiotherapy showed the smallest tumor size (less than 10 mm diameter). In particular, the size of secondary tumor was significantly decreased even though the secondary tumor was not treated with radiation in case of triple combined therapy of the PI3Kγ δ inhibitor, PD-1 blockade and RT inhibitor.

The macroscopic observation result demonstrates the triple combination treatment of the present invention could significantly inhibit growth of secondary tumor as well as primary tumor.

Comparative Example 1. Size of Tumor in Immunodeficient Mouse

An immunodeficient animal model was prepared in substantially the same manner as in Example 4-1 by using nude mouse (BALB/c-nude female mice, CAnN.Cg-Foxn1nu/Cr1jOri; Orient Bio, Inc.). The animal model was grouped into 7 groups and treated in the same manner as Example 4-1.

The macroscopic images of primary and secondary tumors in immunodeficient mouse model are shown in FIG. 7b. The secondary tumor size was not changed according to treatment methods in immunodeficient mouse model.

The result demonstrates that the triple combined therapy of the PI3K-γ or PI3K-δ inhibitor, PD-1 blockade and RT inhibitor have systemic effect by regulating immune cells in tumor microenvironment.

The invention claimed is:

1. A method of treating triple negative breast cancer, comprising
administering a therapeutically effective amount of
1) a PI3K inhibitor against one or more selected from the group consisting of PI3K delta and PI3K gamma, and
2) a PD-1 blockade; and
performing radiotherapy,
wherein the PI3K inhibitor is one or more selected from the group consisting of duvelisib, tenalisib and idelalisib, wherein the PD-1 blockade is one or more selected from the group consisting of pembrolizumab and nivolumab, wherein the triple negative breast cancer is one selected from the group consisting of (i) metastatic tumor, (ii) metastatic tumor and primary tumor, (iii) metastatic tumor and recurrent tumor, and (iv) metastatic tumor, primary tumor and recurrent tumor.

2. The method according to claim 1, wherein the step of administering the PI3K inhibitor and the PD-1 blockade is performed by mixing the PI3K inhibitor and the PD-1 blockade and administering them together, or by administering the PI3K inhibitor and the PD-1 blockade simultaneously or sequentially.

3. The method according to claim 1, wherein the radiotherapy is performed at a dosage of 8 to 12 Gy in 1 to 5 times fractions (Fx), at an irradiation interval of 1 to 3 days.

4. The method according to claim 1, wherein the method reduces the tumor volume of a subject to 0.25 times or less of the tumor volume in a no-treatment control group.

5. The method according to claim 1, wherein the method increases the ratio of CD8 positive cells in tumor tissue to 2 times to 100 times compared to a no-treatment control group.

6. The method according to claim 1, wherein the method of treatment reduces the ratio of regulatory T cells ($T_{reg}$) in tumor tissue to 60% or less than a no-treatment control group, and the ratio of myeloid-derived suppressor cells (MDSC) to 90% or less than a no-treatment control group.

7. The method according to claim 1, wherein the method of treatment reduces the ratio of M2 tumor-associated macrophages (M2 TAM) in tumor tissue to 50% or less than a no-treatment control group, and increases the ratio of M1 tumor-associated macrophages (M1 TAM) to 1.1 to 3 times compared to a no-treatment control group.

* * * * *